(12) United States Patent
Fisher et al.

(10) Patent No.: US 7,141,368 B2
(45) Date of Patent: Nov. 28, 2006

(54) MULTI-DIRECTIONAL DEPOSITION IN ARRAY FABRICATION

(75) Inventors: William D. Fisher, San Jose, CA (US); Peter G. Webb, Menlo Park, CA (US); Svetlana V. Shchegrova, Campbell, CA (US); Michael P. Caren, Palo Alto, CA (US)

(73) Assignee: Agilent Technologies, Inc., Santa Clara, CA (US)

( * ) Notice: Subject to any disclaimer, the term of this patent is extended or adjusted under 35 U.S.C. 154(b) by 227 days.

(21) Appl. No.: 10/066,518

(22) Filed: Jan. 30, 2002

(65) Prior Publication Data

US 2003/0143756 A1    Jul. 31, 2003

(51) Int. Cl.
| | |
|---|---|
| C12Q 1/06 | (2006.01) |
| C12M 1/36 | (2006.01) |
| G01N 15/06 | (2006.01) |
| B01L 3/02 | (2006.01) |
| C07J 21/04 | (2006.01) |

(52) U.S. Cl. .................. 435/6; 435/174; 435/283.1; 435/287.2; 422/68.1; 422/100; 536/23.1

(58) Field of Classification Search .............. 435/6, 435/7.1, 174, 283.1, 287.2; 422/68.1, 100
See application file for complete search history.

(56) References Cited

U.S. PATENT DOCUMENTS

| | | |
|---|---|---|
| 4,380,017 A | 4/1983 | Ort |
| 5,486,452 A * | 1/1996 | Gordon et al. ............. 435/5 |
| 6,063,339 A * | 5/2000 | Tisone et al. .............. 422/67 |
| 6,171,797 B1 | 1/2001 | Perbost |
| 6,180,351 B1 | 1/2001 | Cattell |
| 6,228,659 B1 * | 5/2001 | Kowallis et al. ........... 436/180 |
| 6,232,072 B1 | 5/2001 | Fisher |
| 6,242,266 B1 | 6/2001 | Schleifer et al. |
| 6,323,043 B1 | 11/2001 | Caren et al. |
| 6,599,693 B1 * | 7/2003 | Webb .......................... 435/4 |
| 6,613,893 B1 * | 9/2003 | Webb ....................... 536/25.3 |

FOREIGN PATENT DOCUMENTS

| | | |
|---|---|---|
| GB | 2 355 716 | 5/2001 |
| WO | WO 99/34931 | 7/1999 |

OTHER PUBLICATIONS

Academic Press Dictionary of Science and Technology, Morris, ed., Academic Press, 1992, p. 1828.*

* cited by examiner

*Primary Examiner*—B J Forman

(57) ABSTRACT

A method, apparatus, and computer program products for fabricating multiple chemical arrays on a substrate, each array having multiple rows of feature locations with arrays of different sets being arranged in a sideways orientation with respect to the rows. The method includes dispensing drops from a drop dispensing head onto the substrate while maintaining a gap between the head and substrate and moving them relative to one another along a path so as to fabricate the arrays. The path for the relative moving includes moving the head in a direction along the rows of a first array set then moving the head in an opposite direction along the rows of a second array set. This pattern is repeated with the second array set of an earlier cycle being the first array set of a later cycle.

20 Claims, 6 Drawing Sheets

MULTI-DIRECTIONAL DEPOSITION IN ARRAY FABRICATION

FIELD OF THE INVENTION

This invention relates to arrays, particularly polynucleotide arrays such as DNA arrays, which are useful in diagnostic, screening, gene expression analysis, and other applications.

BACKGROUND OF THE INVENTION

Polynucleotide arrays (such as DNA or RNA arrays), are known and are used, for example, as diagnostic or screening tools. Such arrays include regions of usually different sequence polynucleotides arranged in a predetermined configuration on a substrate. These regions (sometimes referenced as "features") are positioned at respective locations ("addresses") on the substrate. The arrays, when exposed to a sample, will exhibit an observed binding pattern. This binding pattern can be detected upon interrogating the array. For example all polynucleotide targets (for example, DNA) in the sample can be labeled with a suitable label (such as a fluorescent compound), and the fluorescence pattern on the array accurately observed following exposure to the sample. Assuming that the different sequence polynucleotides were correctly deposited in accordance with the predetermined configuration, then the observed binding pattern will be indicative of the presence and/or concentration of one or more polynucleotide components of the sample. Biopolymer arrays can be fabricated by depositing previously obtained biopolymers (such as from synthesis or natural sources) onto a substrate, or by in situ synthesis methods. Methods of depositing obtained biopolymers include dispensing droplets to a substrate from dispensers such as pin or capillaries (such as described in U.S. Pat. No. 5,807,522) or such as pulse jets (such as a piezoelectric inkjet head, as described in PCT publications WO 95/25116 and WO 98/41531, and elsewhere). The substrate is coated with a suitable linking layer prior to deposition, such as with polylysine or other suitable coatings as described, for example, in U.S. Pat. No. 6,077,674 and the references cited therein.

For in situ fabrication methods, multiple different reagent droplets are deposited from drop dispensers at a given target location in order to form the final feature (hence a probe of the feature is synthesized on the array substrate). The in situ fabrication methods include those described in U.S. Pat. No. 5,449,754 for synthesizing peptide arrays, and described in WO 98/41531 and the references cited therein for polynucleotides. The in situ method for fabricating a polynucleotide array typically follows, at each of the multiple different addresses at which features are to be formed, the same conventional iterative sequence used in forming polynucleotides from nucleoside reagents on a support by means of known chemistry. This iterative sequence is as follows: (a) coupling a selected nucleoside through a phosphite linkage to a functionalized support in the first iteration, or a nucleoside bound to the substrate (i.e. the nucleoside-modified substrate) in subsequent iterations; (b) optionally, but preferably, blocking unreacted hydroxyl groups on the substrate bound nucleoside; (c) oxidizing the phosphite linkage of step (a) to form a phosphate linkage; and (d) removing the protecting group ("deprotection") from the now substrate bound nucleoside coupled in step (a), to generate a reactive site for the next cycle of these steps. The functionalized support (in the first cycle) or deprotected coupled nucleoside (in subsequent cycles) provides a substrate bound moiety with a linking group for forming the phosphite linkage with a next nucleoside to be coupled in step (a). Final deprotection of nucleoside bases can be accomplished using alkaline conditions such as ammonium hydroxide, in a known manner.

The foregoing chemistry of the synthesis of polynucleotides is described in detail, for example, in Caruthers, *Science* 230: 281–285, 1985; Itakura et al., *Ann. Rev. Biochem.* 53: 323–356; Hunkapillar et al., *Nature* 310: 105–110, 1984; and in "Synthesis of Oligonucleotide Derivatives in Design and Targeted Reaction of Oligonucleotide Derivatives", CRC Press, Boca Raton, Fla., pages 100 et seq., U.S. Pat. No. 4,458,066, U.S. Pat. No. 4,500,707, U.S. Pat. No. 5,153,319, U.S. Pat. No. 5,869,643, EP 0294196, and elsewhere. Suitable linking layers on the substrate include those as described in U.S. Pat. No. 6,235,488 and 6,258,454 and the references cited therein.

Further details of fabricating biopolymer arrays by depositing either previously obtained biopolymers or by the in situ method are disclosed in U.S. Pat. No. 6,242,266, U.S. Pat. No. 6,232,072, U.S. Pat. No. 6,180,351, and U.S. Pat. No. 6,171,797.

In array fabrication, the quantities of polynucleotide or other biopolymer available, whether by deposition of previously obtained biopolymer or by in situ synthesis, are usually very small and expensive. Additionally, sample quantities available for testing are usually also very small and it is therefore desirable to simultaneously test the same sample against a large number of different probes on an array. These conditions require use of arrays with large numbers of very small, closely spaced features. It is important in such arrays that features actually be present, that they are put down accurately in the desired target pattern and do not overlap, are of the correct size, and that the biopolymer is uniformly coated within the feature. Failure to meet such quality requirements can have serious consequences to diagnostic, screening, gene expression analysis or other purposes for which the array is being used. However, for economical mass production of arrays with many features it is desirable that they can be fabricated in a short time while maintaining quality.

It is desirable then to provide a means by which arrays can be rapidly fabricated while still maintaining good quality.

SUMMARY OF THE INVENTION

The present invention realizes that in fabricating multiple arrays on a substrate by dispensing drops from one or more dispensers in a dispenser head, a relative path of movement of the head to the substrate should be kept low. Unnecessarily long paths increase the time required to fabricate arrays.

The present invention then provides in one aspect a method of fabricating multiple chemical arrays on a substrate, each array having multiple rows of feature locations with arrays of different sets being arranged in a sideways orientation with respect to the rows. The method includes dispensing drops from a drop dispensing head onto the substrate while maintaining a gap between the head and substrate and moving them relative to one another along a path. The path includes moving the head in a direction along the rows of a first array set, then moving the head in an opposite direction along the rows of a second array set. This movement may be repeated with the second array set of an earlier cycle serving as the first array set of a later cycle. The arrays fabricated may be biopolymer or other chemical arrays.

The foregoing repeating movement may be with a same two array sets or each repetition may be with a new second array set (each second array set may or may not be adjacent the first array set of the same cycle). Furthermore, after the foregoing repeating, the entire path (including the foregoing repetitions) may then again be repeated with the head optionally being re-loaded with fluid between repetitions of the path. As a result, when the path is repeated, the repetitions may be parallel and offset in the sideways orientation from one another.

The present invention further provides an apparatus for fabricating a chemical array. The apparatus includes a head with one or more drop dispensers (such as pulse jets), a transport system to move the head relative to the substrate while maintaining a gap therebetween, and a processor. The processor co-ordinates dispensing of droplets and movement of the deposition system, in accordance with one or more methods of the present invention, and may also control other movements of the head (such as re-loading between repetitions of the path). The apparatus may also include a cutter to separate the substrate into units each of which carries at least one of the arrays. A printer may further be provided, which adds array identifiers to the substrate each in proximity with a corresponding array. The present invention may also further provide for exposing the array to a sample, and reading the array following the exposure and optionally processing results from the reading. Results (processed or not) may be forwarded to a remote location.

The present invention further provides a computer program product for use with an apparatus as described above, and which provides the instructions to the processor such that it can cause the head and transport system to execute one or more methods of the present invention. The program product includes a computer readable storage medium having a computer program stored thereon which, when loaded into a computer (which is a "processor"), causes it to perform the steps required of it in such that the apparatus can perform a method of the present invention.

The various aspects of the present invention can provide any one or more of the following and/or other useful benefits. For example, rapid array fabrication is possible while allowing drops to be deposited close together while avoiding overlapping of drops deposited for different array features.

BRIEF DESCRIPTION OF THE DRAWINGS

Embodiments of the invention will now be described with reference to the drawings, in which.

To facilitate understanding, the same reference numerals have been used, where practical, to designate elements that are common to the figures.

DETAILED DESCRIPTION OF EMBODIMENTS OF THE INVENTION

Figure 1:
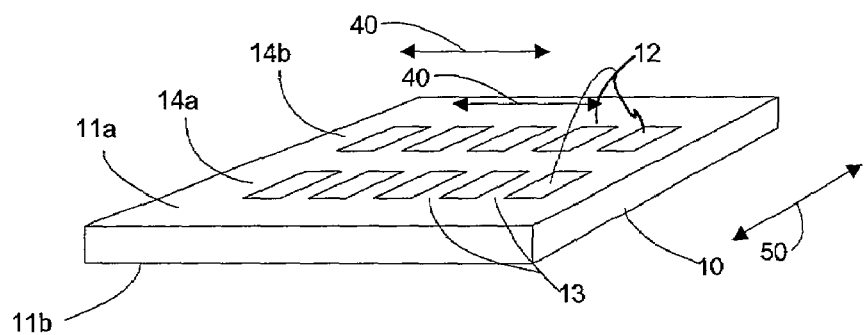
FIG. 1 illustrates a substrate carrying multiple arrays, such as may be fabricated by methods of the present invention.

In the present application, unless a contrary intention appears, the following terms refer to the indicated characteristics. A "biopolymer" is a polymer of one or more types of repeating units. Biopolymers are typically found in biological systems and particularly include polysaccharides (such as carbohydrates), and peptides (which term is used to include polypeptides, and proteins whether or not attached to a polysaccharide) and polynucleotides as well as their analogs such as those compounds composed of or containing amino acid analogs or non-amino acid groups, or nucleotide analogs or non-nucleotide groups. This includes polynucleotides in which the conventional backbone has been replaced with a non-naturally occurring or synthetic backbone, and nucleic acids (or synthetic or naturally occurring analogs) in which one or more of the conventional bases has been replaced with a group (natural or synthetic) capable of participating in Watson-Crick type hydrogen bonding interactions. Polynucleotides include single or multiple stranded configurations, where one or more of the strands may or may not be completely aligned with another. A "nucleotide" refers to a sub-unit of a nucleic acid and has a phosphate group, a 5 carbon sugar and a nitrogen containing base, as well as functional analogs (whether synthetic or naturally occurring) of such sub-units which in the polymer form (as a polynucleotide) can hybridize with naturally occurring polynucleotides in a sequence specific manner analogous to that of two naturally occurring polynucleotides. For example, a "biopolymer" includes DNA (including cDNA), RNA, oligonucleotides, and PNA and other polynucleotides as described in U.S. Pat. No. 5,948,902 and references cited therein (all of which are incorporated herein by reference), regardless of the source. An "oligonucleotide" generally refers to a nucleotide multimer of about 10 to 100 nucleotides in length, while a "polynucleotide" includes a nucleotide multimer having any number of nucleotides. A "biomonomer" references a single unit, which can be linked with the same or other biomonomers to form a biopolymer (for example, a single amino acid or nucleotide with two linking groups one or both of which may have removable protecting groups). A "peptide" is used to refer to an amino acid multimer of any length (for example, more than 10, 10 to 100, or more amino acid units). A biomonomer fluid or biopolymer fluid reference a liquid containing either a biomonomer or biopolymer, respectively (typically in solution).

A "pulse jet" is a device which can dispense drops in the formation of an array. Pulse jets operate by delivering a pulse of pressure (such as by a piezoelectric or thermoelectric element) to liquid adjacent an outlet or orifice such that a drop will be dispensed therefrom. A "drop" in reference to the dispensed liquid does not imply any particular shape, for example a "drop" dispensed by a pulse jet only refers to the volume dispensed on a single activation. A drop which has contacted a substrate is often referred to as a "deposited drop" or the like, although sometimes it will be simply referenced as a drop when it is understood that it was previously deposited. Detecting a drop "at" a location, includes the drop being detected while it is traveling between a dispenser and that location, or after it has contacted that location (and hence may no longer retain its original shape) such as capturing an image of a drop on the substrate after it has assumed an approximately circular shape of a deposited drop.

A "set" or "sub-set" of any item (such as a set of arrays) may contain only one of the item, or only two, or three, or any multiple number of the items. An "array", unless a contrary intention appears, includes any one, two or three dimensional arrangement of addressable regions bearing a particular chemical moiety to moieties (for example, biopolymers such as polynucleotide sequences) associated with that region. An array is "addressable" in that it has multiple regions of different moieties (for example, different polynucleotide sequences) such that a region (a "feature" or "spot" of the array) at a particular predetermined location (an "address") on the array will detect a particular target or class of targets (although a feature may incidentally detect non-targets of that feature). Array features are typically, but need not be, separated by intervening spaces. In the case of an array, the "target" will be referenced as a moiety in a mobile phase (typically fluid), to be detected by probes ("target probes") which are bound to the substrate at the various regions. However, either of the "target" or "target probes" may be the one which is to be evaluated by the other (thus, either one could be an unknown mixture of polynucleotides to be evaluated by binding with the other). An "array layout" refers collectively to one or more characteristics of the features, such as feature positioning, one or more feature dimensions, and some indication of a moiety at a given location. "Hybridizing" and "binding", with respect to polynucleotides, are used interchangeably.

When one item is indicated as being "remote" from another, this is referenced that the two items are at least in different buildings, and may be at least one mile, ten miles, or at least one hundred miles apart. "Communicating" information references transmitting the data representing that information as electrical signals over a suitable communication channel (for example, a private or public network). "Forwarding" an item refers to any means of getting that item from one location to the next, whether by physically transporting that item or otherwise (where that is possible) and includes, at least in the case of data, physically transporting a medium carrying the data or communicating the data.

It will also be appreciated that throughout the present application, that words such as "top", "upper", and "lower" are used in a relative sense only. "Fluid" is used herein to reference a liquid. Reference to a singular item, includes the possibility that there are plural of the same items present. Furthermore, when one thing is "moved", "moving", "repositioned", "scanned", or the like, with respect to another, this implies relative motion only such that either thing or both might actually be moved in relation to the other. For example, when dispensers are "moved" relative to a substrate, either one of the dispensers or substrate may actually be put into motion by the transport system while the other is held still, or both may be put into motion. All patents and other cited references herein, are specifically incorporated into this application by reference except insofar as any may conflict with the present application (in which case the present application prevails).

Figure 2:
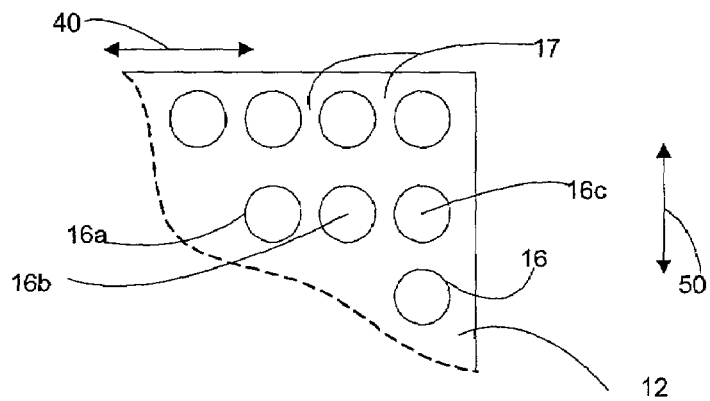
FIG. 2 is an enlarged view of a portion of FIG. 1 showing ideal spots or features.
Figure 3:
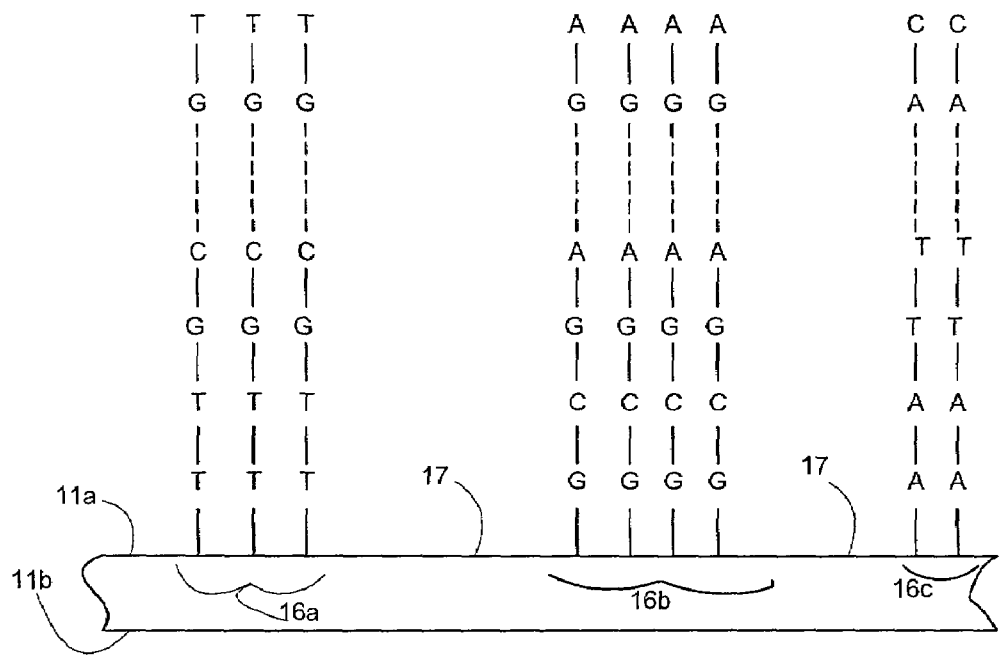
FIG. 3 is an enlarged illustration of a portion of the substrate in FIG. 2.

Referring first to FIGS. 1–3, typically methods and apparatus of the present invention generate or use a contiguous planar substrate 10 carrying one or more arrays 12 disposed across a front surface 11a of substrate 10 and separated by inter-array areas 13. A back side 11b of substrate 10 does not carry any arrays 12. The arrays on substrate 10 can be designed for testing against any type of sample, whether a trial sample, reference sample, a combination of them, or a known mixture of polynucleotides (in which latter case the arrays may be composed of features carrying unknown sequences to be evaluated). While ten arrays 12 are shown in FIG. 5 and the different embodiments described below may use substrates with particular numbers of arrays, it will be understood that substrate 10 and the embodiments to be used with it, may use any number of desired arrays 12. Arrays on any same substrate 10 may all have the same array layout, or some or all may have different array layouts. Similarly, substrate 10 may be of any shape, and any apparatus used with it adapted accordingly. Depending upon intended use, any or all of arrays 12 may be the same or different from one another and each will contain multiple spots or features 16 of biopolymers in the form of polynucleotides. A typical array may contain from more than ten, more than one hundred, more than one thousand or ten thousand features, or even more than from one hundred thousand features. All of the features 16 may be different, or some could be the same (for example, when any repeats of each feature composition are excluded the remaining features may account for at least 5%, 10%, or 20% of the total number of features). As best seen in FIG. 2, features 16 are arranged in straight line rows extending left to right in FIG. 2 along an orientation 40, while arrays 12 may also be arranged in straight line rows 14a, 14b. Each row of arrays 12 may be regarded as an array set 14a, 14b and as seen from FIG. 1, such sets 14a, 14b are arranged in a sideways orientation 50 with respect to the orientation 40 of the rows of features 16 (specifically, as columns orthogonal to the array and feature rows of FIGS. 1–5). In the case where arrays 12 are formed by the conventional in situ or deposition of previously obtained moieties, as described above, by depositing for each feature a droplet of reagent in each cycle such as by using a pulse jet such as an inkjet type head, interfeature areas 17 will typically be present which do not carry any polynucleotide or moieties of the array features. It will be appreciated though, that the interfeature areas 17 could be of various sizes and configurations. It will also be appreciated that there need not be any space separating arrays 12 from one another although there typically will be. Each feature carries a predetermined polynucleotide (which includes the possibility of mixtures of polynucleotides). As per usual, A, C, G, T represent the usual nucleotides. It will be understood that there may be a linker molecule (not shown) of any known types between the front surface 11a and the first nucleotide.

Features 16 can have widths (that is, diameter, for a round spot) in the range from a minimum of about 10 µm to a maximum of about 1.0 cm. In embodiments where very small spot sizes or feature sizes are desired, material can be deposited according to the invention in small spots whose width is in the range about 1.0 µm to 1.0 mm, usually about 5.0 µm to 500 µm, and more usually about 10 µm to 200 µm. Spot sizes can be adjusted as desired, by using one or a desired number of pulses from a pulse jet to provide the desired final spot size. Features which are not round may have areas equivalent to the area ranges of round features 16 resulting from the foregoing diameter ranges. The probes of features 16 are typically linked to substrate 10 through a suitable linker, not shown.

For the purposes of the above description of FIGS. 1–3 and the discussions below, it will be assumed (unless the contrary is indicated) that the array being formed in any case is a polynucleotide array formed by the deposition of previously obtained polynucleotides using pulse jet deposition units. However, the described methods are applicable to arrays of other polymers or chemical moieties generally, whether formed by multiple cycle in situ methods or deposition of previously obtained moieties, or using other types of dispensers, will be understood from these discussions. It will be understood that when methods such as an in situ fabrication method are used, additional steps may be required (such as oxidation and deprotection in which the substrate 10 is completely covered with a continuous volume of reagent).

Figure 4:
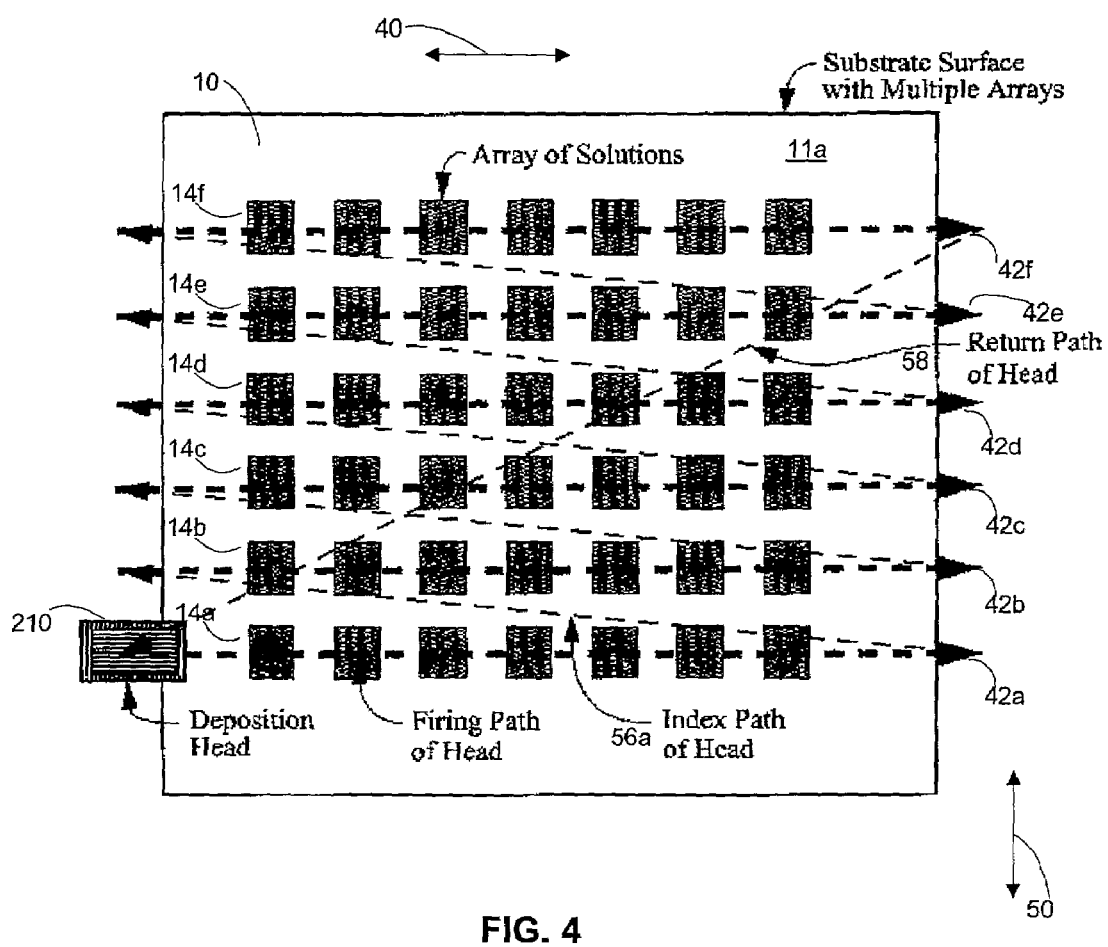
FIG. 4 illustrates one method of fabricating multiple arrays.

Referring now to FIG. 4 there is illustrated one method of fabricating arrays by depositing drops containing a chemical moiety (such as a previously obtained polynucleotide or peptide). In the illustrated method multiple array sets 14a to 14f are to be fabricated. Note that in FIGS. 4 through 7 the arrays being fabricated are the same as those described in connection with FIGS. 1–3 (there are just more of them shown on a substrate 10 in FIGS. 4, 6, 7). To do this the drops are dispensed from a drop dispensing head 210 while maintaining a gap between the head and substrate and moving them relative to one another along a path. This path includes moving the head in a first direction 42a along the feature rows of a first set of arrays 14a (that is along the orientation 40). Head 210 is then moved in a direction 56a to return to the left hand side of substrate 10 (as viewed in FIG. 4) but positioned for travel over a second set of arrays 14b, over which it is moved in a direction 42b. The foregoing cycle of movement is repeated but with head 210 moving over each of the array sets 14c to 14f in turn. However, the foregoing movement of head 210 is inefficient in that each time head 210 is returned to the left side of substrate 210 along direction 56a, no drop dispensing takes place and time is therefore wasted.

Figure 5A:
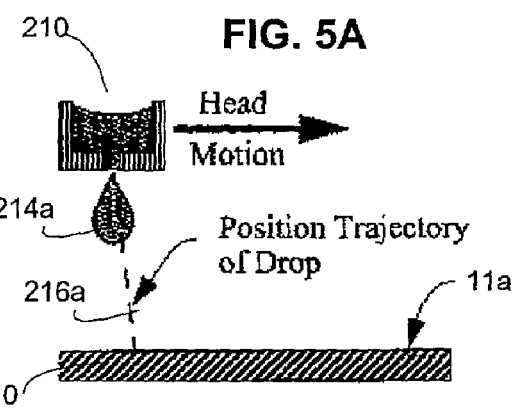
FIG. 5 illustrates how dispensing drops from a head moving in different directions in different passes, can result in overlap (which includes merging) of drops deposited for different array features.
Figure 5B:
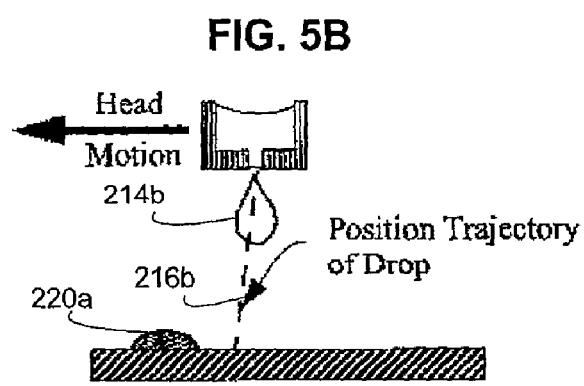
Figure 5C:
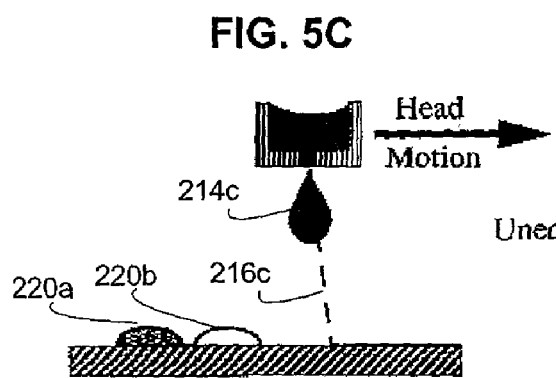
Figure 5D:
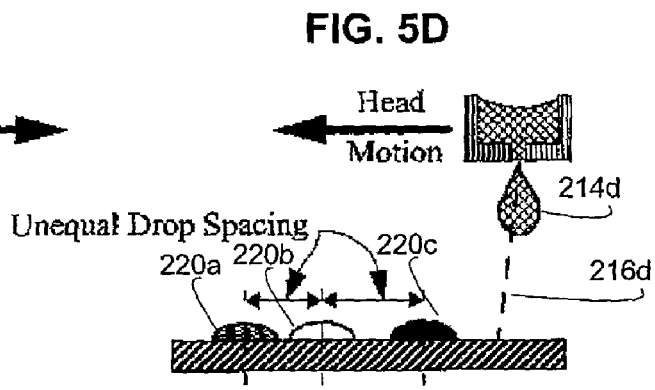

However, the present invention recognizes that in array fabrication it is not desirable to simply move head 210 back and forth in opposite directions in different passes along over a set (row) of arrays. The reason for this is illustrated in FIG. 5 which for simplicity shows dispensing of drops 214a through 214d from a single dispenser in head 210 during successive passes (FIG. 5A to 5D) over a same row of arrays. Note the trajectories 216a through 216d of dispensed drops 214a through 214d will be at an angle to a surface 11b of substrate 10, with the drops traveling in a same direction through the gap between head 210 and surface 11b as the head 210 is traveling when the drops are dispensed. As best seen in FIG. 5D, this results in uneven spacing of deposited drops on surface 11b. Consequently, when trying to fabricate an array with features as close as possible, there is a risk drops for different features may overlap. Even if one maintains a spacing between deposited drops sufficiently large to avoid this (which is wasteful of space on the substrate 10 and hence requires more of a sample to cover the surface), the features 16 would still be unevenly spaced. This makes interpretation of the results from reading the array difficult, since software used to automatically recognize feature 16 images typically assumes the features are evenly spaced.

Figure 6:
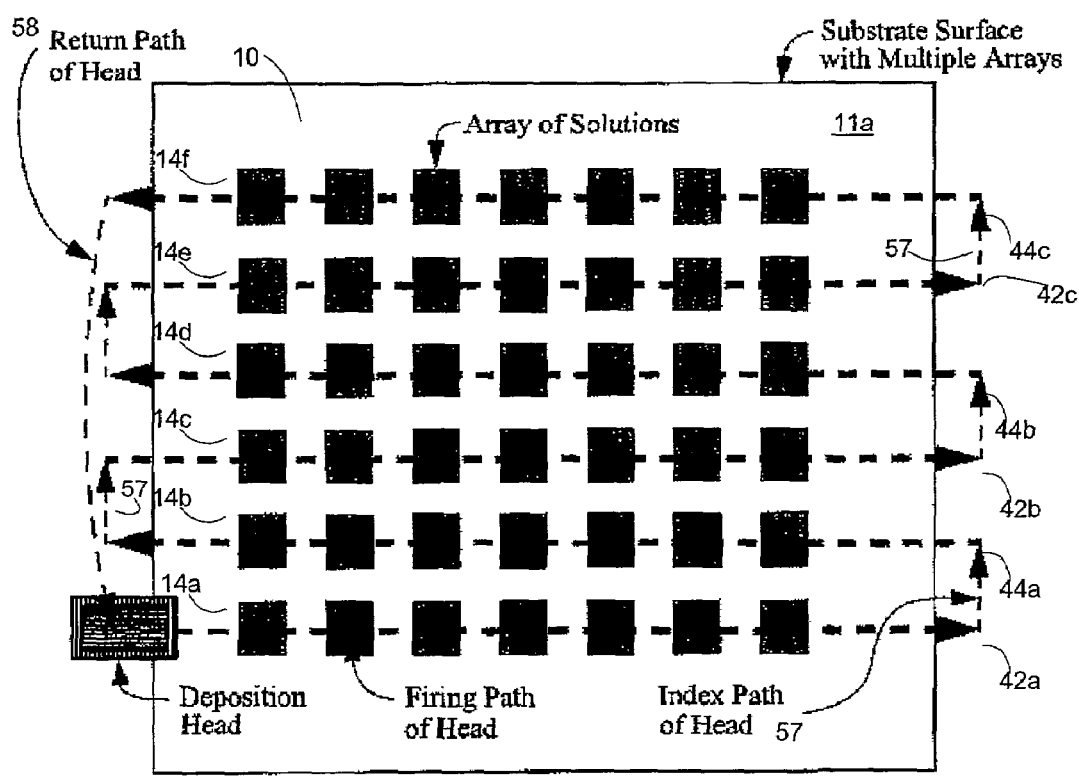
FIG. 6 illustrates a relative head movement path of the present invention.
Figure 7:
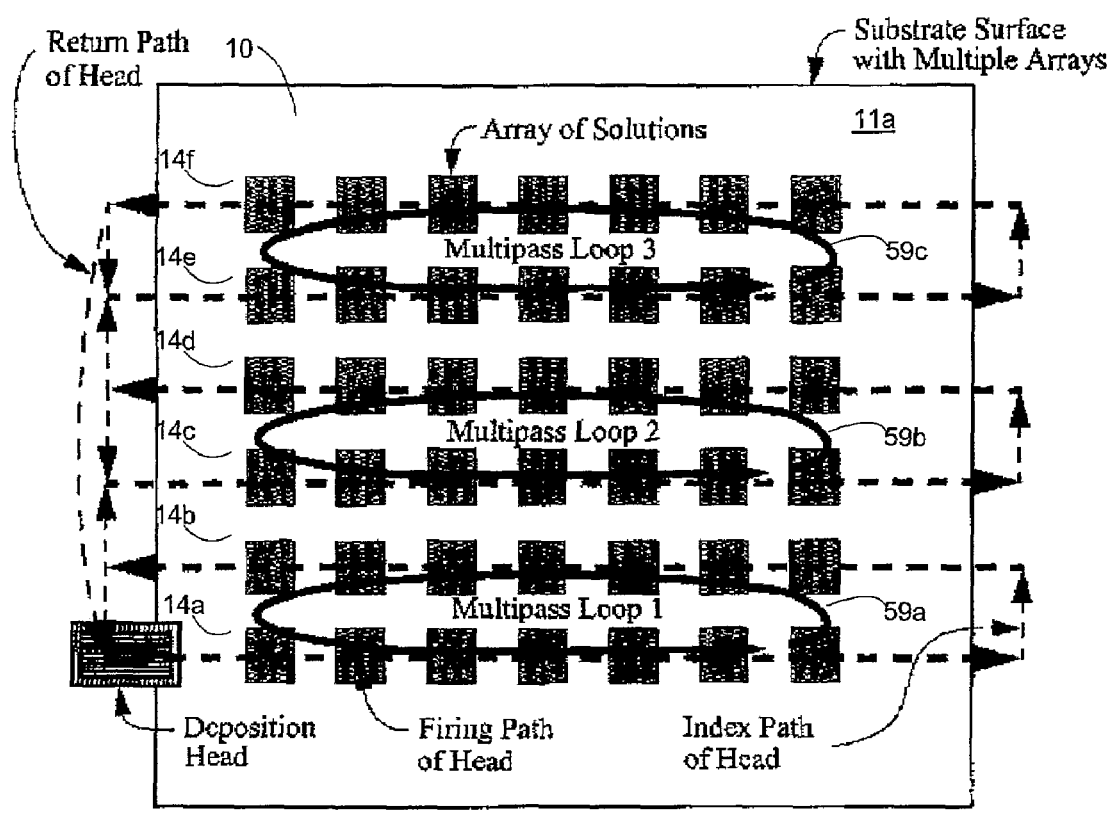
FIG. 7 illustrates another relative head movement path of the present invention

FIG. 6 illustrates a method of the present invention. As before, drops are dispensed from a head 210 onto the surface 11b of substrate 10 while maintaining a gap between the head and substrate. However, in FIG. 6 head 210 and substrate 10 are moved relative to one another along a different path than in FIG. 5. In particular, the path for the relative moving while dispensing in FIG. 5 includes moving the head in a first direction 42a along the rows of first array set 14a (that is, along the orientation 40), then moving the head in an opposite direction 44a along the rows of a second array set 14b. Note that the movement in the opposite direction over the next array set is performed without any intervening movement of head 210 in the opposite direction 44a over any or all of the first array set 14a (that is, in FIG. 5 head 210 moves in the opposite direction 44a over set 14b without any intervening movement in first direction 42a over first set 14a). Also, between these movements in the opposite directions head 210 is displaced in the sideways orientation 57 between one array set 14 and the next while not dispensing any drops. As seen in FIG. 6, this displacement occurs between an end of travel of head 210 along one direction for one array set, and the beginning of travel of head 210 along the opposite direction for the next array set 14. The foregoing first cycle is then repeated over each of the remaining array sets 14c through 14f, with the second array set of an earlier cycle being the first array set of a later cycle. For example, in the first cycle array set 14b was the second array set. In the next (third) cycle array set 14c will be the second array set and array set 14b will become the first array set. Note that each new second array set in FIG. 6 is still adjacent and parallel the first array set of the same cycle (for example, in the third cycle array sets 14c and 14d are adjacent to one another) When head 210 has completed the path over all the array sets it can be returned to the lower left-hand corner position shown in FIG. 6. At this point the entire foregoing relative moving path of the head and substrate can be repeated while dispensing drops. Between repetitions of the path though, head 210 can be reloaded with fluids for dispensing, as required by the desired layout of arrays 12 being fabricated. Note that the different repetitions of movement of the head on the path illustrated in FIG. 6 during drop dispensing, are parallel and will typically be offset by some number of array rows (for example at least two, five, ten, or twenty) in the sideways orientation from one another. This allows drops to be deposited for different rows of the arrays during different repetitions of the path.

In another embodiment of the method, the repeating of a cycle with first and second array sets can be with a same two array sets. This is illustrate in FIG. 7 wherein the first, third, and fifth cycles are each repeated multiple times by having head 210 travel in a loop 59a, 59b, 59c over the first and second array sets of respective cycles as many times as desired while depositing drops during the fabrication of the arrays.

The results of the above fabrication methods will be that the majority of the rows in arrays within a set are dispensed while the head is moving in a same direction along the rows. In fact if all the arrays are formed only by dispensing drops during repetitions of the entire path, then all of the rows in all the array sets will have been dispensed while head 210 was moving in the same direction along the rows of each array. However, less desirably, if some features had respective drops deposited while head 210 was moving in some other pattern, it is possible to have at least 60%, 80%, 90%, or 95% of the rows of one or more arrays having had its drops deposited while head 210 was moving in one direction for each one or more arrays.

Figure 8:
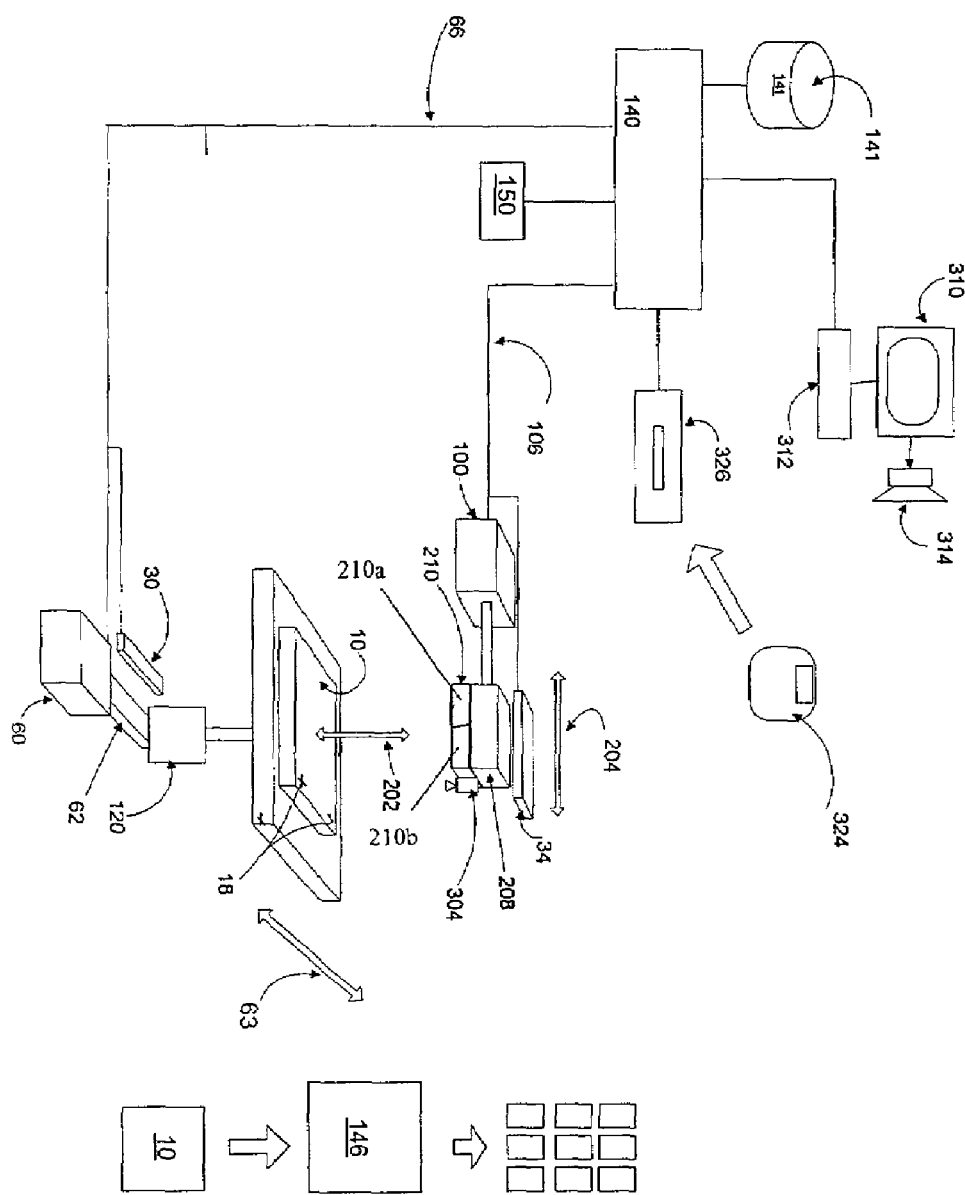
FIG. 8 is a schematic diagram of an apparatus of the present invention which can execute a method of the present invention.

Referring to FIG. 8 an apparatus of the present invention includes a substrate station 20 on which can be mounted a substrate 10. Pins or similar means (not shown) can be provided on substrate station 20 by which to approximately align substrate 10 to a nominal position thereon. Substrate station 20 can include a vacuum chuck connected to a suitable vacuum source (not shown) to retain a substrate 10 without exerting too much pressure thereon, since substrate 10 is often made of glass.

A dispensing head system 210 is retained by a head retainer 208. Head system 210 can be positioned at any position facing substrate 10 by means of a transport system. The transport system includes a carriage 62 connected to a first transporter 60 controlled by processor 140 through line 66, and a second transporter 100 controlled by processor 140 through line 106. Transporter 60 and carriage 62 are used execute one axis positioning of station 20 (and hence mounted substrate 10) facing the dispensing head system 210, by moving it in the direction of nominal axis 63, while transporter 100 is used to provide adjustment of the position of head retainer 208 in a direction of nominal axis 204 (and hence move the rows of dispensers as described in connection with FIGS. 6 and 7). In this manner, head system 210 can be scanned line by line, by scanning along a line over substrate 10 in the direction of axis 204 using transporter 100 while substrate 10 is stationary, while line by line movement of substrate 10 in a direction of axis 63 is provided by transporter 60 while head system 210 is stationary. Head system 210 may also optionally be moved in a vertical direction 202, by another suitable transporter (not shown). However, it will be appreciated that other scanning configurations could be used. Also, it will be appreciated that both transporters 60 and 100, or either one of them, with suitable construction, could be used to perform the foregoing scanning of head system 210 with respect to substrate 10. Thus, when the present application refers to "positioning", "moving", or "displacing" or the like, one element (such as head system 210) in relation to another element (such as one of the stations 20 or substrate 10) it will be understood that any required moving can be accomplished by moving either element or a combination of both of them. An encoder 30 communicates with processor 140 to provide data on the exact location of substrate station 20 (and hence substrate 10 if positioned correctly on substrate station 20), while encoder 34 provides data on the exact location of holder 208 (and hence head system 210 if positioned correctly on holder 208). Any suitable encoder, such as an optical encoder, may be used which provides data on linear position. Angular positioning of substrate station 20 is provided by a transporter 120, which can rotate substrate station 20 about axis 202 under control of processor 140. Typically, substrate station 20 (and hence a mounted substrate) is rotated by transporter 120 under control of processor 140 in response to an observed angular position of substrate 10 as determined by processor 140 through viewing one or more fiducial marks on substrate 10 (particularly fiducial marks 18) with a camera (not shown). This rotation will continue until substrate 10 has reached a predetermined angular relationship with respect to dispensing head system 210. In the case of a square or rectangular substrate, the mounted substrate 10 will typically be rotated to align one edge (length or width) with the scan direction of head system 210 along axis 204.

Head system 210 may contain one or more (for example, two or three) heads mounted on the same head retainer 208. Each such head may be the same in construction as a head type commonly used in an ink jet type of printer. Each ejector is in the form of an electrical resistor operating as a heating element under control of processor 140 (although piezoelectric elements could be used instead). Each orifice with its associated ejector and portion of the chamber, defines a corresponding pulse jet with the orifice acting as a nozzle. It will be appreciated that head system 210 could have any desired number of pulse jets (for example, at least fifty or at least one hundred pulse jets). In this manner, application of a single electric pulse to an ejector causes a droplet to be dispensed from a corresponding orifice. Certain elements of each head can be adapted from parts of a commercially available thermal inkjet print head device available from Hewlett-Packard Co. as part no. HP51645A. One type of head and other suitable dispensing head designs are described in more detail in U.S. patent application entitled "A MULTIPLE RESERVOIR INK JET DEVICE FOR THE FABRICATION OF BIOMOLECULAR ARRAYS" Ser. No. 09/150,507 filed Sep. 9, 1998. However, other head system configurations can be used such as that described in U.S. patent application Ser. No. 10/022088 titled "Multiple Inkjet Die, Multiple Reservoir Printhead Manufacturing Using Single Housing" by Daquino et al. filed Dec. 18, 2001 and owned by the assignee of the present application.

As is well known in the ink jet print art, the amount of fluid that is expelled in a single activation event of a pulse jet, can be controlled by changing one or more of a number of parameters, including the orifice diameter, the orifice length (thickness of the orifice member at the orifice), the size of the deposition chamber, and the size of the heating element, among others. The amount of fluid that is expelled during a single activation event is generally in the range about 0.1 to 1000 pL, usually about 0.5 to 500 pL and more usually about 1.0 to 250 pL. A typical velocity at which the fluid is expelled from the chamber is more than about 1 m/s, usually more than about 10 m/s, and may be as great as about 20 m/s or greater. As will be appreciated, if the orifice is in motion with respect to the receiving surface at the time an ejector is activated, the actual site of deposition of the material will not be the location that is at the moment of activation in a line-of-sight relation to the orifice, but will be a location that is predictable for the given distances and velocities.

The sizes of the features can have widths (that is, diameter, for a round spot) in the range from a minimum of about 10 μm to a maximum of about 1.0 cm. In embodiments where very small spot sizes or feature sizes are desired, material can be deposited according to the invention in small spots whose width is in the range about 1.0 μm to 1.0 mm, usually about 5.0 μm to 500 μm, and more usually about 10 μm to 200 μm. Spot sizes can be adjusted as desired, by using one or a desired number of pulses from a pulse jet to provide the desired final spot size.

The apparatus further includes a sensor in the form of a camera 304, to monitor dispensers for errors (such as failure to dispense droplets) by monitoring for drops dispensed onto substrate 10 when required of a dispenser. Camera 304 communicates with processor 140, and should have a resolution that provides a pixel size of about 1 to 100 micrometers and more typically about 4 to 20 micrometers or even 1 to 5 micrometers. Any suitable analog or digital image capture device (including a line by line scanner) can be used for such camera, although if an analog camera is used processor 140 should include a suitable analog/digital converter. A detailed arrangement and use of such a camera to monitor for dispenser errors, is described in U.S. Pat. No. 6,232,072. Particular observations techniques are described, for example, in co-pending U.S. patent application Ser. No. 09/302,898 filed Apr. 30, 1999 by Caren et al., assigned to the same assignee as the present application, incorporated herein by reference. Alternatively, the sensor can be a drop detector which detects an electrical charge on a dispensed drop, in accordance with the apparatus and methods described in U.S. patent application Ser. No. 09/558,532 entitled "Array Fabrication with Drop Detection" filed by Christopher A. Schantz et al. Monitoring can occur during formation of an array and the information used during fabrication of the remainder of that array or another array, or test-print patterns can be run before array fabrication. A display 310, speaker 314, and operator input device 312, are further provided. Operator input device 312 may, for example, be a keyboard, mouse, or the like. Processor 140 has access to a memory 141, and controls print head system 210 (specifically, the activation of the ejectors therein), operation of the transport system, operation of each jet in print head system 210, capture and evaluation of images from the camera 304, and operation display 310 and speaker 314. Memory 141 may be any suitable device in which processor 140 can store and retrieve data, such as magnetic, optical, or solid state storage devices (including magnetic or optical disks or tape or RAM, or any other suitable device, either fixed or portable). Processor 140 may include a general purpose digital microprocessor suitably programmed from a computer readable medium carrying necessary program code, to execute all of the functions required of the methods of the present invention and as described below. It will be appreciated though, that when a "processor" such as processor 140 is referenced throughout this application, that such includes any hardware and/or software combination which will perform the required functions. Suitable programming can be provided remotely to processor 140, or previously saved in a computer program product such as memory 141 or some other portable or fixed computer readable storage medium using any of those devices mentioned below in connection with memory 141. For example, a magnetic or optical disk 324 may carry the programming, and can be read by disk reader 326.

A cutter 146 is further provided in the apparatus to separate the substrate along two orthogonal sets of parallel lines extending through inter-array areas 13. A printer 150 (such as an inkjet or laser printer) can print array identifiers for attaching to the substrate 10 each in proximity (that is, adjacent to) a corresponding array. Use and application of such identifiers is described in further detail in U.S. Pat. No. 6,180,351 which, as already mentioned, is incorporated herein by reference Operation of the apparatus of FIG. 8 in accordance with a method of the present invention, will now be described. First, it will be assumed that memory 141 holds a target drive pattern. This target drive pattern is the instructions for driving the apparatus components as required to form the target array (which includes target locations and dimension for each spot) on substrate 10 and includes, for example, movement commands to transporters 60 and 100 as well as firing commands for each of the pulse jets in head system 210 co-ordinated with the movement of head system 210 and substrate 10, as well as instructions for which polynucleotide solution (or precursor) is to be loaded in each pulse jet (that is, the "loading pattern"). This target drive pattern is based upon the target array pattern and can have either been input from an appropriate source (such as input device 312, a portable magnetic or optical medium, or from a remote server, any of which communicate with processor 140), or may have been determined by processor 140 based upon an input target array pattern (using any of the appropriate sources previously mentioned) and the previously known nominal operating parameters of the apparatus. Further, it will be assumed that drops of different biomonomer or biopolymer containing fluids (or other fluids) have been placed at respective regions of a loading station (not shown).

Processor 140 causes head 210 to be loaded with different biopolymer or biomonomer (or other biopolymer precursors, such as biopolymer fragments to be linked to one another in situ on substrate 10) containing fluids. A loading sequence for head system 210 is more completely described in U.S. Pat. No. 6,323,043 and U.S. Pat. No. 6,242,266, including the possibility of using a flexible microtitre plate as described in U.S. patent application "Method and Apparatus for Liquid Transfer", Ser. No. 09/183,604. Those references and all other references cited in the present application, are incorporated into this application by reference. Processor 140 can control pressure within head system 210 to load each polynucleotide solution into the chambers in the head by drawing it through the orifices as described in one or more of the foregoing patents or applications. As already mentioned, in this sequence processor 140 will operate the apparatus according to the drive pattern, by causing the transport system to position head system 210 facing substrate station 20, and particularly the mounted substrate 10, and with head system 210 maintained at an appropriate fixed distance (gap) from substrate 10. Processor 140 then controls movement of head 210 while coordinating activation of the ejectors in head 210 to dispense drops therefrom onto substrate 10, in accordance with one or more of the methods described above. As already mentioned, this may include reloading of head 210, and repeating the travel path of head 210 until all drops for the arrays are deposited so as to complete fabrication of the arrays.

At this point the droplet dispensing sequence is complete. The cutter (not shown) may then separates the substrate 10 along two orthogonal sets of parallel lines extending through inter-array areas 13, to provide units 15 carrying at least one array 12. Printer 150 may then print an array identifier onto a label which is applied to the substrate portion of each unit 15 (such as by adhesive) in proximity with a corresponding array, in a manner such as described in U.S. Pat. No. 6,180,351.

Following receipt by a user receives of an array made by an apparatus or method of the present invention, it will typically be exposed to a sample (for example, a fluorescently labeled polynucleotide or protein containing sample) and the array then read. Reading of the array may be accomplished by illuminating the array and reading the location and intensity of resulting fluorescence at each feature of the array,. For example, a scanner may be used for this purpose which is similar to the AGILENT MICROARRAY SCANNER manufactured by Agilent Technologies, Palo Alto, Calif. Other suitable apparatus and methods are described in U.S. patent applications: Ser. No. 09/846125 "Reading Multi-Featured Arrays" by Dorsel et al.; and Ser. No. 09/430214 "Interrogating Multi-Featured Arrays" by Dorsel et al. As previously mentioned, these references are incorporated herein by reference. However, arrays may be read by any other method or apparatus than the foregoing, with other reading methods including other optical techniques (for example, detecting chemiluminescent or electroluminescent labels) or electrical techniques (where each feature is provided with an electrode to detect hybridization at that feature in a manner disclosed in U.S. Pat. No. 6,251,685, U.S. Pat. No. 6,221,583 and elsewhere). Results from the reading may be raw results (such as fluorescence intensity readings for each feature in one or more color channels) or may be processed results such as obtained by rejecting a reading for a feature which is below a predetermined threshold and/or forming conclusions based on the pattern read from the array (such as whether or not a particular target sequence may have been present in the sample, or whether or not a pattern indicates a particular condition of an organism from which the sample came). The results of the reading (processed or not) may be forwarded (such as by communication) to a remote location if desired, and received there for further use (such as further processing).

The present methods and apparatus may be used to deposit biopolymers or other chemical moieties on surfaces of any of a variety of different substrates, including both flexible and rigid substrates. Preferred materials provide physical support for the deposited material and endure the conditions of the deposition process and of any subsequent treatment or handling or processing that may be encountered in the use of the particular array. The array substrate may take any of a variety of configurations ranging from simple to complex. Thus, the substrate could have generally planar form, as for example a slide or plate configuration, such as a rectangular or square or disc. In many embodiments, the substrate will be shaped generally as a rectangular solid, having a length in the range about 4 mm to 1 m, usually about 4 mm to 600 mm, more usually about 4 mm to 400 mm; a width in the range about 4 mm to 1 m, usually about 4 mm to 500 mm and more usually about 4 mm to 400 mm; and a thickness in the range about 0.01 mm to 5.0 mm, usually from about 0.1 mm to 2 mm and more usually from about 0.2 to 1 mm. However, larger substrates can be used, particularly when such are cut after fabrication into smaller size substrates carrying a smaller total number of arrays 12.

In the present invention, any of a variety of geometries of arrays on a substrate 10 may be fabricated other than the rectilinear rows and columns of arrays 12 of FIG. 1. For example, arrays 12 can be arranged in a sequence of curvilinear rows across the substrate surface (for example, a sequence of concentric circles or semi-circles of spots), or in some other arrangement. Similarly, the pattern of features 16 may be varied from the rectilinear rows and columns of spots in FIG. 2 to include, for example, a sequence of curvilinear rows across the substrate surface (for example, a sequence of concentric circles or semi-circles of spots), or some other regular pattern. Even irregular arrangements are possible provided a user is provided with some means (for example, an accompanying description) of the location and an identifying characteristic of the features (either before or after exposure to a sample). In any such cases, the arrangement of dispensers in head system 210 may be altered accordingly. The configuration of the arrays and their features may be selected according to manufacturing, handling, and use considerations.

The substrates will typically be non-porous, and may be fabricated from any of a variety of materials. In certain embodiments, such as for example where production of binding pair arrays for use in research and related applications is desired, the materials from which the substrate may be fabricated should ideally exhibit a low level of non-specific binding during hybridization events. In many situations, it will also be preferable to employ a material that is transparent to visible and/or UV light. For flexible substrates, materials of interest include: nylon, both modified and unmodified, nitrocellulose, polypropylene, and the like, where a nylon membrane, as well as derivatives thereof, may be particularly useful in this embodiment. For rigid substrates, specific materials of interest include: glass, fused silica; plastics (for example, polytetrafluoroethylene, polypropylene, polystyrene, polycarbonate, and blends thereof, and the like); metals (for example, gold, platinum, and the like).

The substrate surface onto which the polynucleotide compositions or other moieties is deposited may be smooth or substantially planar, or have irregularities, such as depressions or elevations. The surface may be modified with one or more different layers of compounds that serve to modify the properties of the surface in a desirable manner. Such modification layers, when present, will generally range in thickness from a monomolecular thickness to about 1 mm, usually from a monomolecular thickness to about 0.1 mm and more usually from a monomolecular thickness to about 0.001 mm. Modification layers of interest include: inorganic and organic layers such as metals, metal oxides, polymers, small organic molecules and the like. Polymeric layers of interest include layers of: peptides, proteins, polynucleic acids or mimetics thereof (for example, peptide nucleic acids and the like); polysaccharides, phospholipids, polyurethanes, polyesters, polycarbonates, polyureas, polyamides, polyethyleneamines, polyarylene sulfides, polysiloxanes, polyimides, polyacetates, and the like, where the polymers may be hetero- or homopolymeric, and may or may not have separate functional moieties attached thereto (for example, conjugated).

Various further modifications to the particular embodiments described above are, of course, possible. Accordingly, the present invention is not limited to the particular embodiments described in detail above.

What is claimed is:

1. A method of fabricating multiple chemical arrays on a substrate, wherein:
   each array of the multiple chemical array has multiple rows of features, wherein the features are separated from each other by inter-feature areas;
   the multiple chemical arrays are separated from each other by inter-array areas, wherein the inter-array areas are of greater width than the inter-feature areas; and
   the multiple chemical arrays are arranged in sets where the arrays of different sets are arranged in an orthogonal orientation with respect to the rows;
   the method comprising dispensing drops onto the substrate from a drop dispensing head positioned such that a gap is maintained between the head arid the substrate while moving the head and substrate relative to one another along a bi-directional path so as to fabricate the arrays, wherein the bi-directional path for the relative moving comprises:
   (a) moving the head in a direction along the rows of a first array set;
   (b) then moving the head in an opposite direction along the rows of a second array set without intervening movement of the head in the opposite direction over all of the first array set; and
   (c) repeating (b), with the second array set of an earlier cycle being the first array set of a later cycle; wherein between movements in the opposite directions, the dispensing head is displaced in a sideways orientation between one array set and the next and a majority of the rows in arrays within a set are dispensed while the head is moving in a same direction along the rows.

2. A method according to claim 1 wherein the chemical arrays are biopolymer arrays.

3. A method according to claim 1 wherein the first and second array sets are adjacent to one another.

4. A method according to claim 1 wherein the repeating in (c) is with a same two array sets.

5. A method according to claim 1 wherein (b) is repeated multiple times each time with a new second array set.

6. A method according to claim 5 wherein each new second array set is adjacent the first array set of the same cycle.

7. A method according to claim 5 additionally comprising then repeating the relative moving path of the head and substrate while dispensing drops.

8. A method according to claim 7 wherein the head is re-loaded with fluid between repetitions of the path.

9. A method according to claim 7 wherein different repetitions of movement of the head on the path during drop dispensing are parallel and offset in the sideways orientation from one another.

10. A method according to claim 1 wherein the rows of features in the arrays are straight lines.

11. A method according to claim 1 wherein the arrays have the same array layout.

12. A method according to claim 1 additionally comprising separating the substrate into units each of which carries at least one of the arrays.

13. A method according to claim 1 additionally comprising adding array identifiers to the substrate each in proximity with a corresponding array.

14. A method according to claim 1 wherein the head has multiple drop dispensers.

15. A method according to claim 14 wherein the drop dispensers are pulse jets.

16. A method of fabricating multiple chemical arrays on a substrate, wherein:
   each array of the multiple chemical array has multiple rows of features, wherein the features are separated from each other by inter-feature areas;
   the multiple chemical arrays are separated from each other by inter-array areas, wherein the inter-array areas are of greeter width than the inter-feature areas; and
   the multiple chemical arrays are arranged in sets where the arrays of different sets are arranged in an orthogonal orientation with respect to the rows;
   the method comprising dispensing drops onto the substrate from a drop dispensing head positioned such that a gap is maintained between the head and the substrate while moving the head and substrate relative to one another along a bi-directional path so as to fabricate the arrays, wherein the bi-directional path for the relative moving comprises:
   (a) moving the head in a direction along the rows of a first array set;
   (b) then moving the head in an opposite direction along the rows of a second array set without intervening movement of the head in the opposite direction over all of the first array set; and
   (c) repeating (b), with the second array set of an earlier cycle being the first array set of a later cycle; and
   wherein 90% of the rows in arrays within a set are dispensed while the head is moving in a same direction along the rows.

17. A method of fabricating multiple chemical arrays on a substrate, wherein:
   each array of the multiple chemical array has multiple rows of features, wherein the features are separated from each other by inter-feature areas;
   the multiple chemical arrays are separated from each other by inter-array areas, wherein the inter-array areas are of greater width than the Inter-feature areas; and
   the multiple chemical arrays are arranged in sets where the arrays of different sets are arranged in an orthogonal orientation with respect to the rows;
   the method comprising dispensing drops onto the substrate from a drop dispensing head positioned such that a gap is maintained between the head and the substrate while moving the head and substrate relative to one another along a bi-directional path so as to fabricate the arrays, wherein the bi-directional path for the relative moving comprises:
   (a) moving the head in a direction along the rows of a first array set;
   (b) then moving the head in an opposite direction along the rows of a second array set without intervening movement of the head in the opposite direction over all of the first array set; and
   (c) repeating (b), with the second array set of an earlier cycle being the first array set of a later cycle; and
   wherein at least 80% of the rows in arrays within a set are dispensed while the head is moving in a same direction along the rows.

18. A method of producing a structure comprising a substrate having multiple chemical arrays present on a surface thereof, wherein (i) each chemical array has multiple features arranged In rows and separated from each other by inter-feature areas; (ii) the multiple chemical arrays are separated from each other by inter-array areas, wherein the Inter-array areas are of greater width than the inter-feature areas; and (iii) the multiple chemical arrays are arranged in sets where the arrays of different sets are arranged in an orthogonal orientation with respect to the rows of features;
   the method comprising:
   (a) moving a drop dispensing head relative to the substrate along the rows of a first set of chemical arrays while dispensing drops onto the substrate;
   (b) moving the drop dispensing head relative to the substrate in an opposite direction of step (a) along the rows of a second array set while dispensing drops onto the substrate without an intervening movement of the dispensing head across the substrate; and
   (c) repeating (b), with the second array set of an earlier cycle being the first array set of a later cycle;
   wherein between movements in the opposite directions, the dispensing head is displaced in a sideways orientation between one array set and the next and a majority of the rows in arrays within a set are dispensed while the head is moving in a same direction along the rows; and
   wherein a structure comprising a substrate having multiple chemical arrays is produced.

19. A method according to claim 18 wherein the chemical arrays are biopolymer arrays.

20. A method according to claim 18 wherein the head has multiple drop dispensers.

* * * * *

UNITED STATES PATENT AND TRADEMARK OFFICE
CERTIFICATE OF CORRECTION

| | | |
|---|---|---|
| PATENT NO. | : 7,141,368 B2 | Page 1 of 1 |
| APPLICATION NO. | : 10/066518 | |
| DATED | : November 28, 2006 | |
| INVENTOR(S) | : Fisher et al. | |

It is certified that error appears in the above-identified patent and that said Letters Patent is hereby corrected as shown below:

In column 14, line 38, in Claim 1, delete "arid" and insert -- and --, therefor.

In column 15, line 31, in Claim 16, delete "greeter" and insert -- greater --, therefor.

In column 15, line 60, in Claim 17, delete "Inter-feature" and insert -- inter-feature --, therefor.

In column 16, line 27, in Claim 18, delete "In" and insert -- in --, therefor.

In column 16, line 30, in Claim 18, delete "Inter-array" and insert -- inter-array --, therefor.

Signed and Sealed this

Twentieth Day of March, 2007

JON W. DUDAS
*Director of the United States Patent and Trademark Office*